United States Patent
Le Comte

(10) Patent No.: US 8,029,732 B2
(45) Date of Patent: Oct. 4, 2011

(54) QUALITY CONTROL DEVICE FOR A BLOOD ANALYSER USING WHOLE BLOOD

(75) Inventor: Roger Le Comte, Perols (FR)

(73) Assignee: Horiba ABX SA, Montpellier (FR)

( * ) Notice: Subject to any disclaimer, the term of this patent is extended or adjusted under 35 U.S.C. 154(b) by 1094 days.

(21) Appl. No.: 10/564,784

(22) PCT Filed: Jul. 7, 2004

(86) PCT No.: PCT/FR2004/001767
§ 371 (c)(1),
(2), (4) Date: May 22, 2006

(87) PCT Pub. No.: WO2005/019835
PCT Pub. Date: Mar. 3, 2005

(65) Prior Publication Data
US 2006/0275177 A1     Dec. 7, 2006

(30) Foreign Application Priority Data

Jul. 21, 2003  (FR) ..................................... 03 08863

(51) Int. Cl.
*G01N 33/00*  (2006.01)
(52) U.S. Cl. ............ 422/73; 422/65; 422/560; 422/562; 422/565
(58) Field of Classification Search .............. 422/63–65, 422/68.1, 102–104, 73, 501, 509, 547, 549, 422/560, 561, 562, 565; 436/43, 47
See application file for complete search history.

(56) References Cited

U.S. PATENT DOCUMENTS

| | | | |
|---|---|---|---|
| 5,578,268 A | 11/1996 | Champseix et al. | |
| 5,646,046 A | 7/1997 | Fischer et al. | |
| 6,335,166 B1 * | 1/2002 | Ammann et al. | ................. 435/6 |
| 2002/0118594 A1 | 8/2002 | Vellinger et al. | |
| 2003/0029254 A1 | 2/2003 | Hvidtfeldt et al. | |
| 2003/0054542 A1 | 3/2003 | Burns et al. | |

FOREIGN PATENT DOCUMENTS

| | | |
|---|---|---|
| EP | 0634660 | 1/1995 |
| EP | 0726453 | 8/1996 |
| EP | 1174717 | 1/2002 |
| WO | 01/36982 | 5/2001 |
| WO | 02/26386 | 4/2002 |

OTHER PUBLICATIONS

U.S. Appl. No. 10/569,647, filed Feb. 27, 2006, Dupoteau et al.

* cited by examiner

*Primary Examiner* — Jill Warden
*Assistant Examiner* — Dwayne K Handy
(74) *Attorney, Agent, or Firm* — Oblon, Spivak, McClelland, Maier & Neustadt, L.L.P.

(57) ABSTRACT

A quality control device for a blood analyzer using whole blood, which specifically can be used to check the correct operation of the blood analyzer. The device includes a storage for storing control bloods by cooling; a mechanism for bringing the control bloods back to the temperature specified by the control blood manufacturer; a stirring mechanism used for resuspension of the cells; and a mechanism for sampling the blood thus prepared.

19 Claims, 4 Drawing Sheets

QUALITY CONTROL DEVICE FOR A BLOOD ANALYSER USING WHOLE BLOOD

The invention relates to haematological analysers intended for automatically analysing samples of blood products.

It relates more particularly to a quality control device for a blood analyser using whole blood.

The term "analyser" will be used below to mean any apparatus capable of carrying out analyses from a tube of blood, serum, plasma or urine.

The expression "analyser of whole blood" will be used to mean an analyser carrying out analyses on whole blood, i.e. containing all the elements of the blood, as opposed to analysers operating on plasma or serum.

The expression "quality control" is used to mean a procedure which consists in checking at least daily that the analyser is working properly before carrying out examinations on patients.

The expression "low, high or normal control blood" is used to mean blood whose values are selected to be rather low, high or normal.

The control bloods intended for analysers are generally presented in a form of "phials" or "tubes" and are proposed with low, normal and high values in order to monitor the instrument over the range of its measuring capacity.

The rules of passage of control bloods depend on legislation. Generally, it is necessary to pass through the normal level, plus one low or high level at least once a day. In certain cases, and in particular for apparatuses which operate night and day, it is necessary to pass at least once the normal level when there is a change of operator.

If we refer to the standard NCCLS H38-P paragraph 5.7.2, the authors refer to the major importance of stirring in the quality control method, in particular relating to the stirring time and the manner of stirring the control bloods. The official recommendations show that better control of the pre-analytic tools is very important for the relevance of quality control.

The storage of control bloods is effected by refrigeration at the temperature recommended by the supplier in order to guarantee the expiry date given by the supplier. They should have resumed the ambient temperature and have been carefully mixed before being passed through the analyser. Restoration to temperature is an important factor in the good functioning of quality control.

The control bloods are supplied with result sheets giving for each level of blood and for each parameter the target value to be obtained and the acceptable limits or tolerances.

The expiry date as well as the maximum number of samples taken from the same tube of control blood are also given by the manufacturer and must be carefully observed.

The results obtained by analysing the control bloods must be archived by the laboratory. They are often presented in the form of graphs known as "Levey Jennings" in order to simplify their interpretation.

The procedure of passing control bloods in a laboratory consists in setting the analyser in operation if necessary, removing the control bloods from a refrigerator, leaving the bloods on a draining board for several minutes so that they adopt the ambient temperature, stirring the control bloods carefully, passing the bloods through the analyser, checking if the results are within the limits given by the manufacturer, and in replacing the bloods in the refrigerator.

In the process, the expiry date must be checked each time and the maximum number of successive uses of the same tube or phial must be observed.

The same procedure is necessary for the use of an apparatus operating night and day in an emergency service or intensive care or even in the field of a dispensary of a doctor located outside the hospital, requiring the operator to remove the bloods from the refrigerator and to carry out the entire procedure described above. In the field of the usages given above, the operators are often not well qualified and trained to reproduce the regulatory control procedures necessary to the monitoring of the analyser.

An important phase in the procedure of quality control is placing the quality control back in suspension which requires devices conceived to effect regular, non-aggressive stirring of the phials.

In particular, from US 2002/0118594A1, a stirring device is known having an electromagnet and a small rod contained in the phial. The movement of the electromagnet makes the rod contained in the phial move and brings about stirring in the form of a vortex of blood inside the phial. Apart from the fact that this device requires manual operations in order to be incorporated in a quality control procedure, the principle of stirring which it puts in place has a certain number of associated risks in terms of cells which may be damaged during stirring.

Also, from WO 08501797A1, a stirring device is known which operates by rocking which equips in particular the automatic devices of the firm Beckman Coulter. In this device, cassettes containing the control tubes are loaded horizontally on a conveyor belt subjected to a rocking motion which permits stirring of the blood.

Also known from U.S. Pat. No. 5,110,743 is a stirring device operating by inversion, consisting of a disc which may receive tubes. The disc is composed of two sub-units which may start to rotate independently of one another. One disc is used for stirring and the other for storage.

The stirring processes using rocking and inversion may be retained as a principle of stirring for quality control. In no case do the patents cited above describe the use of these principles of stirring for an integrated quality control function such as is described in the present application.

Numerous patents describe the quality control composition and place at the forefront qualities of stability and monitorable parameters. This applies for example to the patents U.S. Pat. Nos. 5,529,933, 6,403,377 and 6,448,085. However, none of the patents describes a stirring method or procedure of passing quality control tubes whereby it is possible to reproduce in an optimum manner the stirring and storage of the quality control samples in the analyser.

Given the importance of quality control both in the legislative context and in the context of ensuring the quality of analyses returned to patients, one of the purposes of the invention is to incorporate the quality control in the analysers and to make the process totally automatic in order to eliminate errors linked to handling.

Having been totally freed from quality control, the operator can give all his attention to the patients' results.

The quality control procedure can thus be undertaken by the analyser which carries it out automatically, only the frequency of quality controls and the number and selection of levels of control bloods being programmable by the operator.

This object is achieved by the invention which proposes an automatic quality control device incorporated in a blood analyser operating on whole blood.

To carry out a quality control for checking the correct functioning of the analyser, the device according to the invention comprises means of storage by refrigeration of the control bloods, means of bringing the control bloods back to the temperature prescribed by the manufacturer of the control bloods, stirring means for the re-suspension of the cells, and means of sampling the blood thus prepared.

According to a first feature, the storage means of the control blood comprise a specified number of tubes closed with a bung and arranged in a support in contact with the refrigeration block for regulating the temperature and maintaining an optimum temperature for the storage of the control blood.

In the invention, the cooling of control bloods and the restoration to temperature thereof form essential operations for achieving quality control in optimum conditions.

Advantageously, the refrigeration block is a refrigeration block operating by the Peltier effect which makes it possible to control the temperature of the block by means of electronic control means. It will be recalled that such a block is supplied with electric current and permits precise control of the temperature. It is furthermore low in bulk, which favours its incorporation in an analyser.

However, the invention is not limited to the use of a Peltier effect refrigeration block, and other types of refrigeration block are conceivable within the scope of the invention.

For restoring to temperature, various solutions are proposed.

First of all, and whatever the type of refrigeration block used, the tube support can be disconnected from the refrigeration block for restoring the temperature of the control bloods.

In the case of a Peltier effect refrigeration block, the current supplying the Peltier effect refrigeration block may be interrupted for a specified period of time in order to restore the control bloods to temperature. The cut-out of current causes a rise in the temperature of the refrigeration block to the ambient value.

Still in the case of a Peltier effect refrigeration block, another solution consists in a command to restore and maintain the quality control at its utilisation temperature according to the specifications of the manufacturer. Then the Peltier effect is used in reverse in order to bring about heating instead of refrigeration.

The stirring means are preferably stirring means operating by rocking and/or inversion formed by the tube support, articulated about a hinge of the refrigeration block. Preferably, the angle of inversion is between 100° and 180°.

According to a second feature, the blood sampling means are formed by a needle capable of drawing blood from the tubes. The needle is actuated by a transverse movement over the tubes of blood to be analysed and control bloods as well as over rinsing and mixing tanks and by a vertical movement to penetrate into the tubes by piercing of the bungs or to be lowered into the rinsing and mixing tanks in order to effect rinsing or dilutions of the blood.

The piercing of the bungs is effected when the tubes on their support are in a high and/or low position.

The device advantageously comprises programmable processing means for checking that the values obtained by running each quality control correspond to the limit values and the values expected of the control blood.

The processing means trigger an alarm if the values obtained during passage of the quality control are outside expected limits.

The device further comprises means of triggering the quality control procedure either directly by an operator or automatically or by an external connection to a control centre.

The transfer and analysis of the data are effected via an internal or external network implementing the standards currently in force, among which can be cited HL7, ASTM and XML.

The tubes preferably comprise means of identification and tracking by way of barcodes, electronic chips and/or magnetic label.

The application of the device according to the invention to analysers of whole blood is novel. It requires the incorporation of storage means for the control bloods, and of mixing and sampling from the sample in the analyser.

In another aspect, the invention relates to a blood analyser comprising a device such as defined above.

In the description below, given by way of example, we refer to the attached drawings, which show:

FIG. 1, a perspective view of a tube support in contact with a refrigeration block according to the invention;

FIG. 2, a view showing the displacement of the support for tubes in FIG. 1 in their stirring movement;

Figure 1:
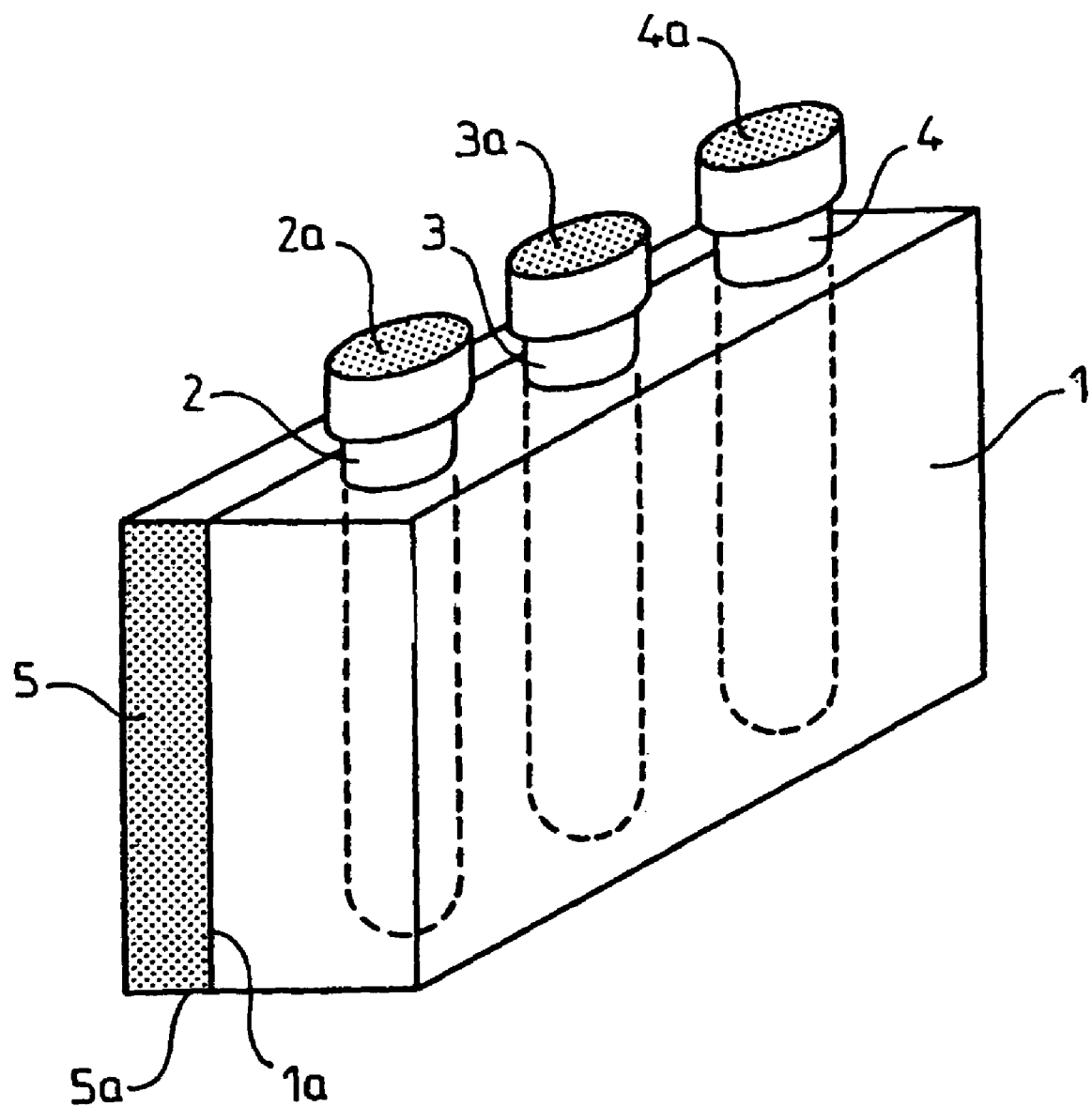

The tube support having the shape of a rectangular parallelepiped, referenced 1 in FIG. 1, comprises three cylindrical housings with longitudinal axes parallel to one another in which are arranged three tubes of control blood 2, 3, 4 sealed by bungs 2a, 3a, 4a. The tubes 2, 3, 4 enclosing control bloods are refrigerated through the support 2 by a refrigeration block 5. The bloods contained in the tubes 2, 3, 4 may correspond to low, normal and high control levels but it is conceivable that there are two or three identical levels or that only one level will be used.

The refrigeration block 5 in the form of a rectangular parallelepiped is in close contact via one of its faces 5a with a face 1a opposite the tube support 1 when the quality control is not in use, i.e. in the rest position, in order to keep the bloods at the temperature recommended by the supplier.

Advantageously, the block 5 may be a refrigeration block operating according to the principle of the Peltier effect, whereby it is possible to control the temperature of the block by means of electronic regulation not shown, the reheating of the tubes taking place for example by interrupting the current passing through the refrigeration block. However, any other method of refrigeration may equally well be used. Thus it is possible also to use the Peltier effect in reverse in order to bring about heating of the tubes and therefore restoration of the temperature of the control bloods.

The tube support 1 is formed from a metal or any other material which conducts heat so that it can rapidly assume the temperature of the refrigeration block and therefore adjust the temperature of the control bloods to the same temperature as that of the refrigeration block.

Figure 2:
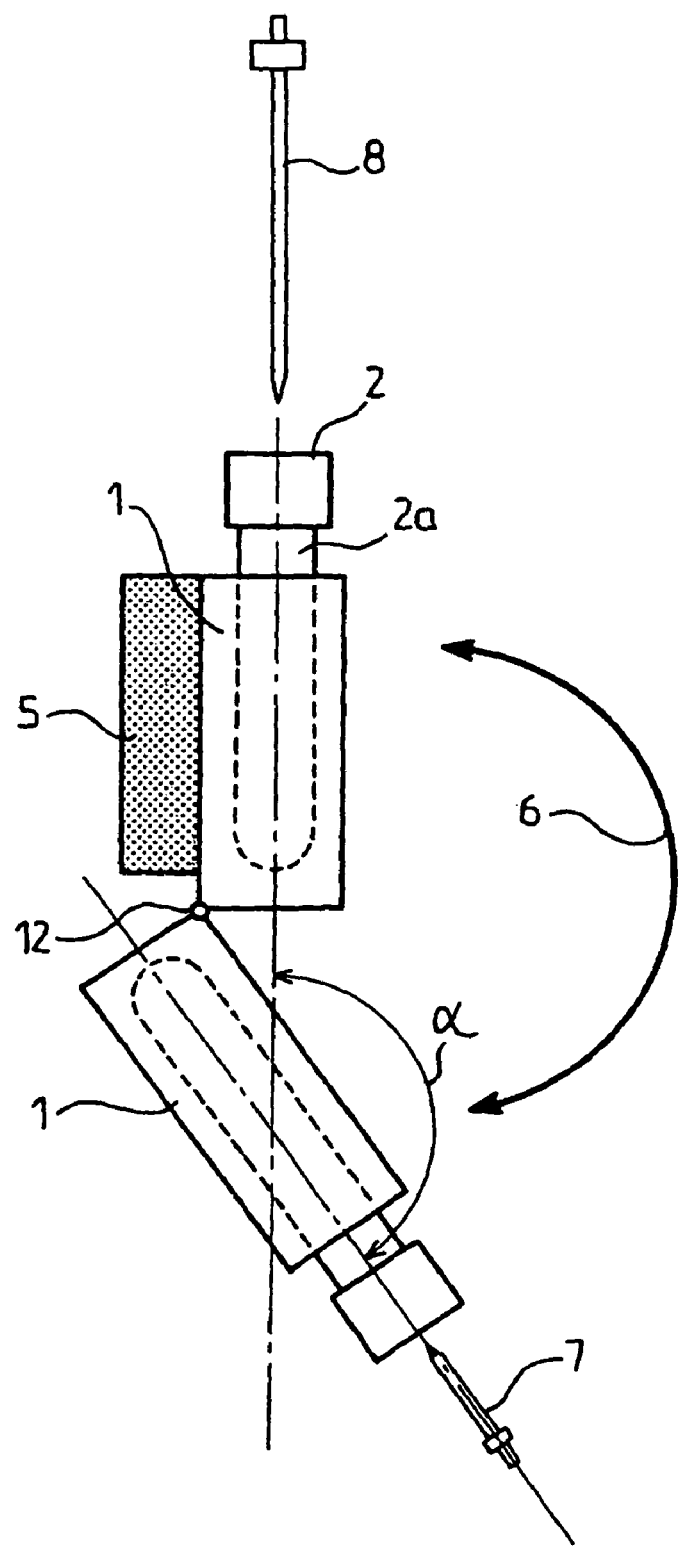

As FIG. 2 shows, where elements corresponding to those of FIG. 1 are shown with the same references, the stirring of the blood is effected by repeated inversion of the tubes 2, 3, 4 about a hinge 12, disposed substantially horizontally, from a high position for which the tubes are oriented vertically with the bungs 2a, 3a, 4a at the top to a low position for which the tubes of blood 2, 3, 4 are oriented vertically but have their bungs 2a, 3a, 4a at the bottom and vice versa. The angle α of inversion may be any and may be for example between 100° and 180°. The mechanical means allowing this movement to be carried out are within reach of the person skilled in the art and are not shown. The alternative movement shown by the double arrow 6 is repeated several times in order to obtain stirring of the blood according to the specifications given by the supplier of the control bloods.

In this preferred embodiment, obviously it is possible to take a sample of the blood with the tube in the high position by sampling means represented by a needle 8 or with the tube in the low position by sampling means represented by a needle 7.

It can also be seen that a rapid restoration of temperature of the control bloods can be obtained by disconnecting the tube support 1 from the refrigeration block 5 by rotation through the angle α about the hinge 12. This solution may be also applied to refrigeration blocks which do not operate by the Peltier effect.

Figure 3A:
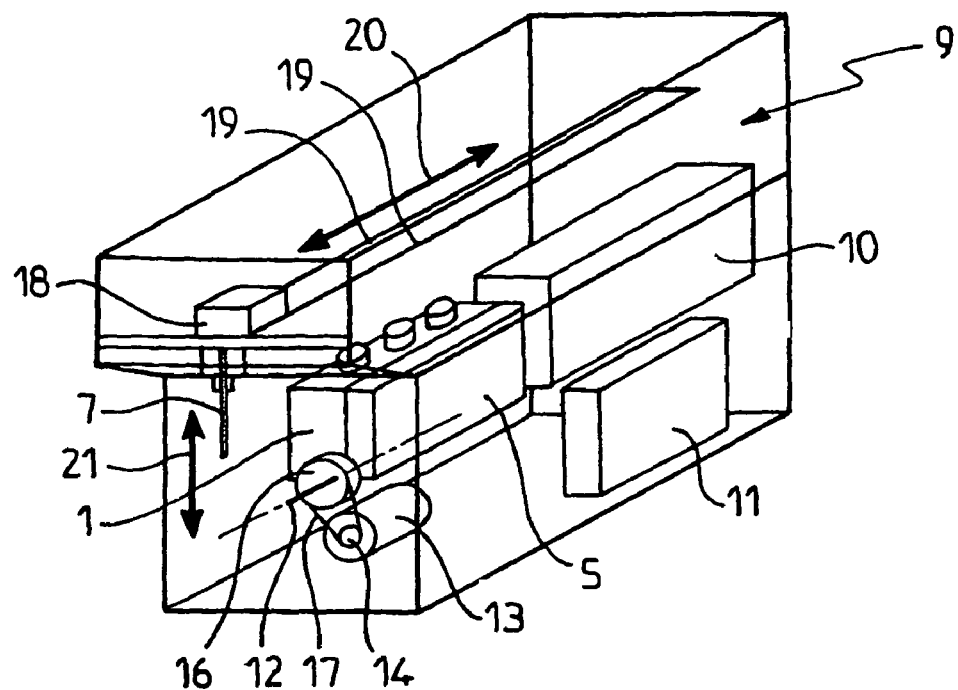
FIGS. 3A and 3B are respectively views in perspective and in front elevation of a quality control device incorporated in an analyser operating on whole blood according to the invention.
Figure 3B:
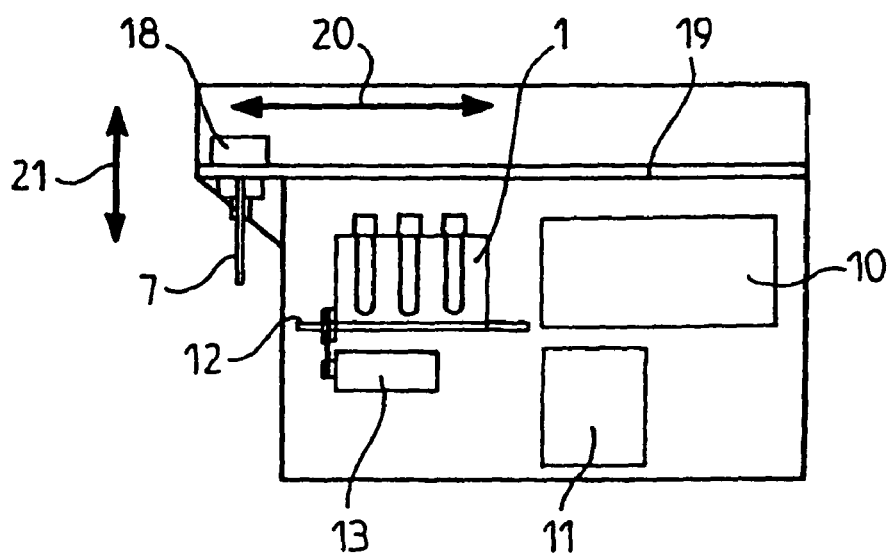

We now refer to FIGS. 3A and 3B which show an example of a quality control device incorporated into an instrument for analysing whole blood 9. The example refers to a cell counter of the type of that described for example in the patent FR 97 13503 registered in the name of the Applicant.

The control device comprises a tube support block 1 in contact with a Peltier effect refrigeration block 2, a sampling needle 7, and a counting block 10 comprising mixing and rinsing tanks (not shown). Also shown in FIGS. 3A and 3B is the electricity supply block of the analysing instrument 9.

The tube support block 1 is driven in rotation about the hinge shaft 12 which is coupled to a motor 13 via a reducing gear formed by a drive pulley 14 connected to the shaft of the motor 13 and via a guided pulley 16 which is connected to the hinge shaft 12, the guided pulley 16 being driven by the drive pulley 14 via a belt 17.

The sampling needle 7 is connected to a carriage 18 which is mobile in translation on two rails 19 which allow it to move in a horizontal movement represented by the double arrow 20, successively over the blood of patients to be analysed, the control bloods contained in the tubes 4, 5, 6 and then the counting block 10 comprising the mixing and rinsing tanks. The displacement of the carriage 18 can be effected by any known means, not shown, such as for example an electric motor of the stepper type, incorporated in the carriage 18 controlled by a microprocessor.

The sampling needle 7 is also actuated in a vertical movement represented by the double arrow 21 which allows it to be lowered into the tubes 2, 3, 4 in order to sample blood or to be lowered into the counting block 10 comprising mixing and rinsing tanks 10 for carrying out rinsing or dilution of blood. The movement of the needle 7 can be effected by an electric stepper-type motor, not shown, coupled for example to a rack supporting the needle 7.

An access door not shown allows the control tubes to be replaced when these are empty or reach their expiry date.

The arrangement of the tubes of control blood is not limited just to the representation in FIGS. 3A and 3B, in which the stirring means shown are only given by way of example. One can also use low-speed Vortex stirring means, those using rocking and/or inversion of the tubes, of the types cited in the prior art, by adapting the refrigeration means to them which are necessary for storage and restoration to temperature of the tubes.

The sampling means may make it necessary to have a sampling method operating with the tube inverted, i.e. with the bung in the lower position. This is often so with analysers using a sampling valve. The rotation of all the quality controls in the stirrer allows the two piercing configurations, it being possible to effect piercing by movement of the needle 7 towards the quality control, or by movement of part or all of the apparatus linked to the quality control towards the needle 7.

Figure 4:
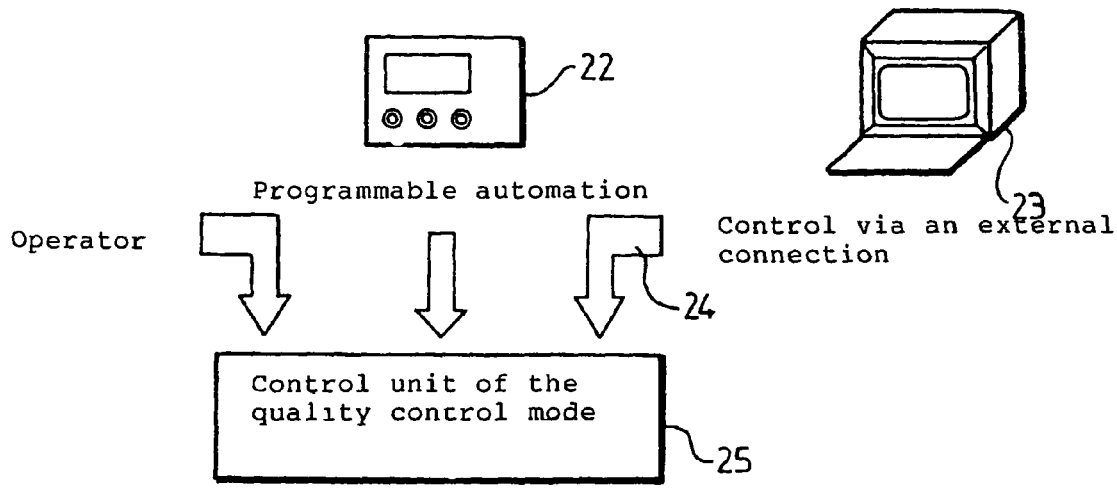
FIG. 4 is a diagram illustrating the modes of operation of the quality control device according to the invention.

As can be seen in FIG. 4, the launching of quality control can be effected in three different ways. It can be launched either by an operator, or automatically by means of a programmable automaton 22 following programming which makes it possible for example to launch quality control in the morning or at night, or by a console 23 via an Intranet or Internet network 24 implementing for example the network technologies known under the designations HL7, ASTM and XML in order to allow a central laboratory, on which the whole blood analyser depends, to launch the quality control procedure. These three modes of launch are managed via a unit 25 which makes it possible to trigger the quality control mode.

Figure 5:
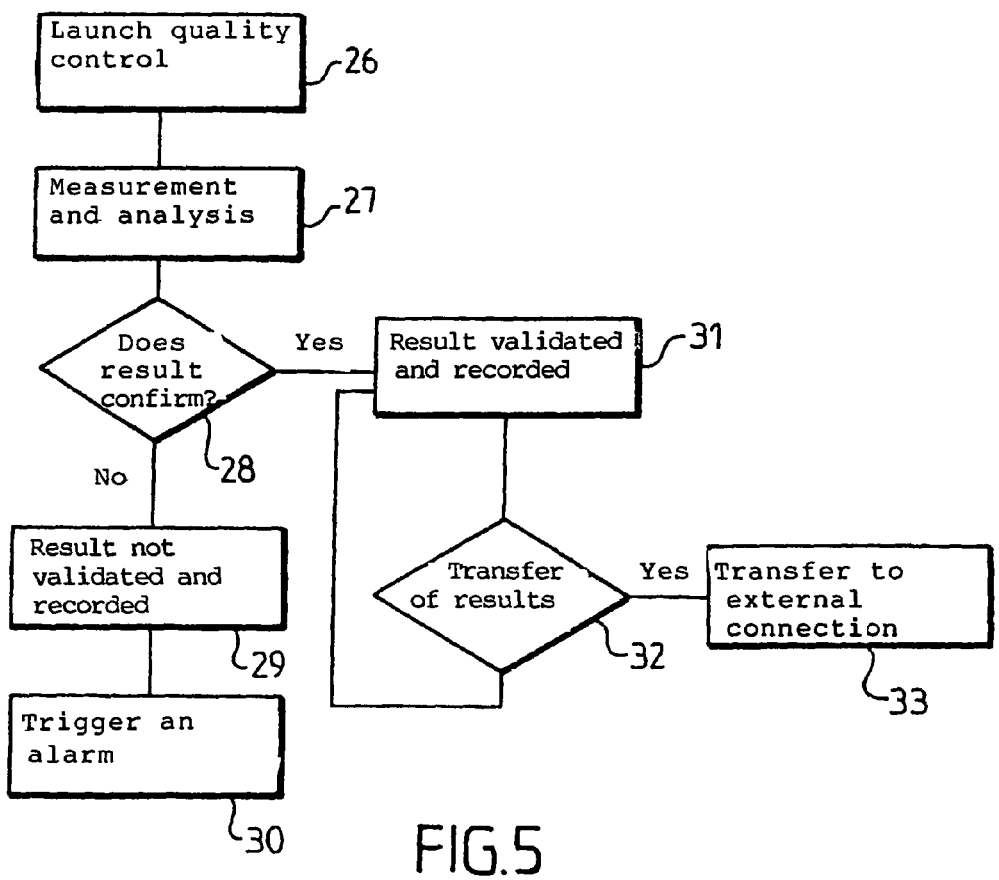
FIG. 5 is a diagram illustrating in the form of a flowchart the process of interpretation and validation of the results obtained by the device according to the invention.

The algorithm shown by stages 26 to 33 of the flowchart in FIG. 5 makes it possible to interpret and validate results and to generate alarms if the quality control is defective. The procedure starts at stage 26 with the launch of the control sequence, which implies the restoration to temperature and stirring of the quality control. The next stage 27 shows the stage of measurement and analysis. At stage 28, a comparison is carried out between the results of the analysis and the values expected of the quality control. If the results are not correct, these are not validated and the stage 29 makes it possible to record data, temporarily to stop the analyser 9 and to trigger an alarm at stage 30.

If at stage 28 the results of the analysis are correct, the results are recorded at stage 31 and according to a test carried out on connection means at stage 32, the results are sent to a server via external connection functions 33.

In this procedure, the identification and tracking of the blood being examined is carried out by any known identification means such as barcode, electronic chip and/or magnetic label accompanying the tubes.

The invention claimed is:

1. A blood analyzer for analyzing whole blood which includes a quality control device, said blood analyzer comprising:
   means for analyzing patient blood samples;
   a quality control device including,
      means for storing by refrigeration control bloods,
      means for restoring the control bloods to a temperature prescribed by a manufacturer of the control bloods,
      means for stirring the control bloods for re-suspension of cells, and means for sampling the control bloods,
   wherein the means for stirring includes a tube support articulated about a hinge and configured to operate by inverting.

2. A blood analyzer according to claim 1, wherein the means for storing control bloods includes a specified number of tubes sealed by a bung and arranged in the tube support in contact with a refrigeration block configured to adjust temperature and maintain an optimum temperature for storing the control bloods.

3. A blood analyzer according to claim 2, wherein the refrigeration block is a Peltier effect refrigeration block.

4. A blood analyzer according to claim 2, wherein the means for restoring the temperature of the control bloods includes the tube support configured to disconnect from the refrigeration block.

5. A blood analyzer according to claim 3, wherein the means for restoring includes the Peltier effect refrigeration block configured to receive current which is interrupted for a specified period of time such that the temperature of the control bloods is restored.

6. A blood analyzer according to claim 3, wherein the Peltier effect refrigeration block is controlled to be reset and maintain quality control to a utilization temperature according to specifications of the manufacturer.

7. A blood analyzer according to claim 2, wherein the hinge is a hinge of the refrigeration block.

8. A blood analyzer according to claim 7, wherein an angle of inversion of the tube support is between 100° and 180°.

9. A blood analyzer according to claim 1, wherein the means for stirring includes low-speed Vortex stirring means.

10. A blood analyzer according to claim 1, wherein the means for sampling includes a needle configured to draw blood from tubes.

11. A blood analyzer according to claim 10, wherein the needle is configured to be driven in a transverse movement over tubes of patient blood samples to be analyzed and the control bloods as well as over a counting block comprising mixing and rinsing tanks and is configured to be driven in a vertical movement to penetrate into the tubes by piercing bungs or by descending into the counting block comprising mixing and rinsing tanks to carry out rinsing or dilutions.

12. A blood analyzer according to claim 11, wherein the bungs are configured to be pierced when the tubes on a support are in a high or low position.

13. A blood analyzer according to claim 1, further comprising programmable processing means for checking that values obtained by passing through a quality control procedure correspond to limit values and expected values of the control blood.

14. A blood analyzer according to claim 13, wherein the processing means triggers an alarm when the values obtained during running of the quality control procedure are outside the expected values.

15. A blood analyzer according to claim 1, wherein the quality control device further includes a triggering unit which triggers a quality control procedure to determine whether the analyzer is functioning properly based on a comparison using the control bloods.

16. A blood analyzer according to claim 1, wherein transfer and analysis of data are affected via an internal or external network implementing standards of HL7, ASTM, or XML.

17. A blood analyzer according to claim 2, wherein the tubes include barcodes, electronic chips, or magnetic labels for identifying and tracking the tubes.

18. A blood analyzer according to claim 15, wherein the triggering unit triggers the quality control procedure either directly by an operator input, automatically, or via an external connection to a control unit.

19. A blood analyzer for analyzing whole blood which includes a quality control device, said blood analyzer comprising:
  an analyzing unit which analyzes patient blood samples;
  a quality control device including,
    a storing unit which stores, by refrigeration, control bloods,
    a restoring unit which restores the control bloods to a temperature prescribed by a manufacturer of the control bloods,
    a stirring unit which stirs the control bloods for re-suspension of cells, and a sampling unit which samples the control bloods,
  wherein the stirring unit includes a tube support articulated about a hinge and configured to operate by inverting.

* * * * *